United States Patent
Wang et al.

(10) Patent No.: US 7,593,913 B2
(45) Date of Patent: Sep. 22, 2009

(54) SYSTEMS AND METHOD FOR INTEGRATIVE MEDICAL DECISION SUPPORT

(75) Inventors: Lu-yong Wang, Plainsboro, NJ (US); Daniel Fasulo, Titusville, NJ (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 358 days.

(21) Appl. No.: 11/620,095

(22) Filed: Jan. 5, 2007

(65) Prior Publication Data
US 2007/0168308 A1    Jul. 19, 2007

Related U.S. Application Data

(60) Provisional application No. 60/757,976, filed on Jan. 11, 2006.

(51) Int. Cl.
*G06F 15/00*    (2006.01)
*G06F 15/18*    (2006.01)

(52) U.S. Cl. ..................................................... 706/62

(58) Field of Classification Search .................... 706/62
See application file for complete search history.

(56) References Cited

U.S. PATENT DOCUMENTS

| | | | |
|---|---|---|---|
| 6,556,977 B1 * | 4/2003 | Lapointe et al. | 706/15 |
| 6,678,669 B2 * | 1/2004 | Lapointe et al. | 706/15 |
| 6,787,525 B1 * | 9/2004 | Schott et al. | 514/45 |
| 7,027,627 B2 * | 4/2006 | Levin et al. | 382/128 |
| 7,228,295 B2 * | 6/2007 | Lapointe et al. | 706/21 |
| 2004/0242972 A1 * | 12/2004 | Adak et al. | 600/300 |
| 2007/0094188 A1 * | 4/2007 | Pandya et al. | 706/45 |

* cited by examiner

*Primary Examiner*—Michael B Holmes

(57) ABSTRACT

A system for providing medical decision support for diagnosis and treatment of disease comprises a medical knowledge database comprising medical information, the medical information including probabilities of disease outcomes for a disease of interest, a memory device for storing a program, a processor in communication with the memory device, the processor operative with the program to obtain patient information and in vitro test results for a patient, and automatically generate a recommendation for a medical test based on a combination of the patient information, the in vitro test results, and medical information from the medical knowledge database.

22 Claims, 3 Drawing Sheets

SYSTEMS AND METHOD FOR INTEGRATIVE MEDICAL DECISION SUPPORT

CROSS-REFERENCE TO RELATED PATENT APPLICATION

This application claims the benefit of U.S. Provisional Application Serial No. 60/757,976, filed Jan. 11, 2006 and entitled "Integrative Decision Support System for Colon Cancer," the content of which is herein incorporated by reference in its entirety.

BACKGROUND OF THE INVENTION

1. Technical Field

The present disclosure relates to medical decision support systems and, more particularly, to computer-implemented systems and methods for integrating biomedical information and supporting medical decision-making.

2. Discussion of Related Art

Modern biotechnology and medical imaging techniques provide various types of information. For example, medical imaging is generally recognized as important for diagnosis and patient care. In recent years, medical imaging has experienced an explosive growth due to advances in imaging modalities such as X-rays, computed tomography (CT), ultrasound, magnetic resonance imaging (MRI) positron emission tomography (PET) and single photon emission computed tomography (SPECT). These imaging modalities provide noninvasive methods to study internal organs in vivo.

Clinical practice, biomedical research and individualized treatment may be improved by integrating heterogeneous biomedical information. There is a need for database-guided decision support systems for clinicians built upon heterogenous biomedical data resources. For example, systems and methods for integrative medical decision support may accelerate the prevention, detection and cure of cancer.

An integrated healthcare decision support platform for colon cancer, for example, may lead to improved colon cancer diagnosis and treatment. Colon cancer is the second-leading cause of death among cancer patients in the United States. Colon cancer emerges via a multi-step progression at both the molecular and the morphologic levels. It develops as the result of the progressive accumulation of genetic and epigenetic alterations that lead to the transformation of normal colonic epithelium to adenocarcinoma.

To identify the genetic and epigenetic alterations in the disease's progress will provide further targets for the development of new therapies for the prevention and treatment of colon tumors throughout their progression from normal epithelium to adenocarcinoma. Preliminary studies of gene expression levels from colon cancer treatment outcomes indicate that the response of drug and treatment is diverse and heterogeneous. Given the complex and heterogeneous nature of colon cancer, integrated healthcare decision support systems built upon heterogenous biomedical data resources may have a revolutionary effect on cancer clinical practice by leading to a personalized, safer and more efficient approach to medication.

Systems and methods are needed for data integration, fusion, and decision support based on heterogeneous data sources, such as diverse clinical/biomedical data sources.

SUMMARY OF THE INVENTION

According to an exemplary embodiment of the present invention, a system for providing medical decision support for diagnosis and treatment of disease comprises: a medical knowledge database comprising medical information, the medical information including probabilities of disease outcomes for a disease of interest, a memory device for storing a program, a processor in communication with the memory device, the processor operative with the program to: obtain patient information and in vitro test results for a patient, and automatically generate a recommendation for a medical test based on a combination of the patient information, the in vitro test results, and medical information from the medical knowledge database.

According to an exemplary embodiment of the present invention, a computer-implemented method of providing medical decision support for cancer diagnosis and treatment includes: providing a medical knowledge database comprising medical information, the medical information including probabilities of cancer outcomes, obtaining patient information for a patient, determining a likelihood of cancer based on the patient information and medical information from the medical knowledge database, obtaining in vitro test results for the patient, updating the likelihood of cancer based on the in vitro test results and medical information from the medical knowledge database, and generating a recommendation for a medical test based on a combination of the patient information and the updated likelihood of cancer.

According to an exemplary embodiment of the present invention, a system for providing medical decision support for cancer diagnosis and treatment comprises: a medical knowledge database comprising medical information, the medical information including probabilities of cancer outcomes, a memory device for storing a program, a processor in communication with the memory device, the processor operative with the program to: obtain patient information for a patient, determine a likelihood of cancer based on the patient information and medical information from the medical knowledge database, obtain in vitro test results for the patient, update the likelihood of cancer based on the in vitro test results and medical information from the medical knowledge database, and automatically generate a recommendation for a medical test based on a combination of the patient information and the updated likelihood of cancer

BRIEF DESCRIPTION OF THE DRAWINGS

The present invention will become more apparent to those of ordinary skill in the art when descriptions of exemplary embodiments thereof are read with reference to the accompanying drawings.

DESCRIPTION OF EXEMPLARY EMBODIMENTS

Figure 1:
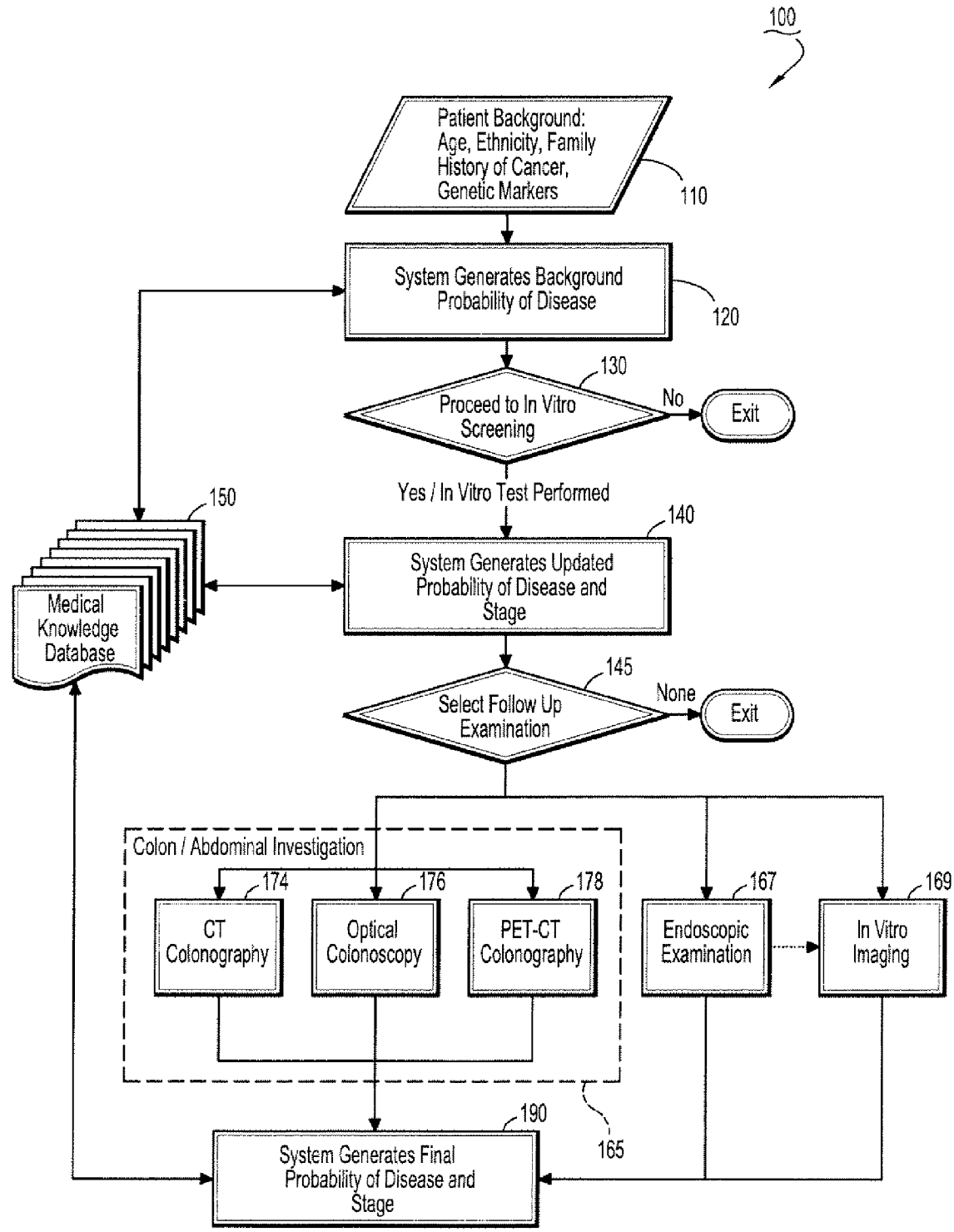
FIG. 1 illustrates a system for providing medical decision support for diagnosis and treatment of disease, according to an exemplary embodiment of the present invention.

Hereinafter, exemplary embodiments of the present invention will be described in detail with reference to the accompanying drawings.

In an exemplary embodiment of the present invention, biomedical information is integrated to help prediction of prognosis and tumor response to specific therapies in cancer treatment, which may allow a personalized, safer and more efficient approach to medication. A systematic view of colon cancer, for example, may be obtained by integrating biomedical information, such as genomics, gene expression levels, protein levels, and clinical and/or epidemiological data.

Molecular imaging may be used to pair diagnosis and therapy. Molecular imaging is useful in cancer, for example, because of the many different molecular mechanisms that can cause cancer. Specific targets may be identified and the information may be utilized to monitor whether the targeted therapy had an effect on the tumor.

In molecular imaging, the PET tracer 2-fluoro-2-D-[18F] fluorodeoxyglucose (FDG), which is biologically equivalent to glucose, can serve as a molecular marker for metabolically hyperactive sites that correspond to tumors. FDG-PET is an accurate and non-invasive way to determine if a mass is malignant. The emerging molecular imaging techniques may be employed to provide in vivo techniques to integrate imaging and genomics.

Molecular imaging can be used to image transcriptional regulation of p53-dependent genes with positron emission tomography in vivo. It can also be used to noninvasively monitor target gene expression by imaging reporter gene expression. In an exemplary embodiment of the present invention, gene expression profiles are used to direct the molecular imaging of colon polyps for cancer early diagnosis and treatment.

An integrative decision support system for cancer treatment, according to an exemplary embodiment of the present invention, integrates heterogeneous biomedical information for improved clinical practice, medical research, and personalized healthcare. For example, colon cancer metastases are moderately hyperintense on T2-weighted images and hypointense on T1-weighted images. The sensitivity of MRI to this type of metastasis can be improved by dynamic contrast-enhanced studies. The metastases from colon cancer derive most of their blood supply from the hepatic artery. Typically the metastases display high signal during the arterial phase and lower signal during the portal venous phase, when the normal hepatic parenchyma, which is supplied primarily by the portal vein, becomes prominent. Ferumoxides are not taken up by metastases. Such tissue-specific contrast agents may aid in preoperative planning.

Various data sources may be integrated for analysis and decision support for cancer treatment. Hereinafter, examples of data sources for cancer treatment will be described.

Genotyping data: Single nucleotide profiles are analyzed on patient population and control. Disease genotype and phenotype association and individual disease or treatment susceptibility can be determined for colon decision support.

Gene expression profiles: Microarray assays monitor thousands of gene expression levels at the same time. They provide a quantitative measurement of the gene expression though the transcription mRNA levels. The profiles can be utilized for analyzing the outcome of the treatment and molecular diagnosis of the disease. In an exemplary embodiment of the present invention, gene expression profiling is used to direct in vivo molecular imaging of colon cancer.

Protein expression profiles: Immunoassays can be used when an unknown concentration of an analyte within a sample needs to be quantified. For example, immunoassays can be used to measure protein concentrations. Immunoassays may be used in screening to quantify the production or inhibition of antigens and haptens related to a disease target.

Mass spectrometry (MS) can be used to probe a large number of protein expression levels at the same time. MS provides a more direct measurement for the functional proteins, and it considers the post-translational modification, which is neglected in microarray technology High-resolution MS, such as liquid chromatography mass spectrometry (LC-MS) may provide more refined information about protein levels in tissue.

Quantitative phenotyping data using virtual colonoscopy: Medical imaging techniques, such as for example, positron emission tomography (PET), magnetic resonance imaging (MRI), and computed tomography (CT), provide noninvasive phenotyping tools. For example, PET, CT or MRI may provide diagnostic tools and phenotyping measurement for colon cancer by imaging the colon polyps. Virtual colonoscopy can be performed with CT, sometimes referred to as a CAT scan, or with MRI, which may provide a good diagnostic tool for colon cancer. Virtual colonoscopy produces two- and three-dimensional images of the colon from the lowest part, the rectum, to the lower end of the small intestine and displays the images on a screen. For example, the procedure may be used to diagnose colon and bowel disease, including polyps, diverticulosis, and colon cancer.

Routine clinical examination data on colon cancer patients may be collected. Biochemical and genetic tests, such as for example, methylated tumor DNA in stool samples, may be used for detecting epigenetic factors.

In an exemplary embodiment of the present invention, a decision support system is based on molecular imaging and clinical data sources using supervised learning algorithms and data fusion techniques. A statistical framework may be used for data fusion. A statistical framework for data fusion may use feature space and supervised learning techniques to build upon the integrated data system of the heterogeneous data sources. Examples of feature space and supervised learning techniques include support vector machine, kernel-based methods, probabilistic boosting tree, etc.

A medical decision support platform for the surgeon/physician, according to an exemplary embodiment of the present invention, includes decision support for individualized treatment based on molecular profiles and phenotypes of colon before or after surgery cancer. To identify multiple loci interaction and identify genetic heterogeneity, boosted generative modeling may be employed.

Diagnostic support and biomarker identification may be based on expression profiling on colon polyps using microarray data or MS.

Heterogeneous data fusion and decision support may be based on microarray data and genotype data, which may be detected by association analysis and data fusion. A decision support system, according to an exemplary embodiment of the present invention, supports analysis and optimization for a series of treatments for colon cancer.

A decision support system for design-tissue and stage-specific agent for molecular imaging may use uses max-specific and min-invasive diagnosis techniques. In an exemplary embodiment of the present invention, gene expression profiling is used to direct in vivo molecular imaging of colon cancer.

A decision support system may utilize a distributed medical knowledge database. The distributed database may be used for biomedical knowledge discovery, including but not limited to: detecting multi-locus interaction network and environmental factors in colon cancer in the genetic heterogenetic population of the United States or other geographical regions, mining genotype-phenotype association in colon cancer and individual susceptibility for colon cancer, mining the association between the genotype and gene expression levels, mining and reverse-engineering the biochemical networks in colon cancer, mining and analysis the gene expression transcription regulation in colon cancer progression, and vertical data integration and mining ranging from genotype, gene expression, proteins, pathways and phenotypes, etc.

FIG. 1 illustrates a system for providing medical decision support for diagnosis and treatment of disease, according to an exemplary embodiment of the present invention.

Referring to FIG. 1, in block 110, patient information for a patient is entered into the system 100 for providing medical decision support. For example, the patient information may include age, ethnicity, family history of disease, genetic markers and/or symptoms. The patient information may include physical and/or physiological findings.

In block 120, the system 100 generates a probability of disease, which is also referred to herein as a "likelihood of disease". The likelihood of disease may be based on the patient information and medical information from a medical knowledge database 150. Examples of a medical knowledge database 150 which will be described later in this disclosure.

For a disease of interest A, the probability of occurrence of the disease A characteristics across the population may be denoted as Pr(A). The disease characteristics may include disease progression (stage), severity, etc. The patient information may be represented by a vector B, herein referred to as patient profile B. The conditional probability Pr(A|B) of occurrence of the disease A given the patient profile B may be expressed as Equation 1.

$$Pr(A \mid B) = \frac{Pr(B \mid A)Pr(A)}{Pr(B)}, \quad (1)$$

where Pr(B|A) is the conditional probability of occurrence of the patient profile B for the disease A, where Pr(A) is the probability of occurrence of the disease A across a the population, and where Pr(B) is the probability of occurrence of the patient profile B across the population.

The medical knowledge database 150 includes medical information, such as for example, probabilities of disease outcomes for a disease of interest. The disease of interest may be a cellular disease, such as cancer. Medical information may include information on diseases, conditions, symptoms, medications, and treatment options and outcomes, risks, and benefits associated therewith. Medical information may include information from case histories, randomized controlled trials, prospective longitudinal cohort studies, retrospective cohort studies, case control studies, cross sectional studies, case series, anecdotes and/or clinical observations. The medical knowledge database 150 may be a distributed database system.

In block 130, the system 100 determines whether to proceed to in vitro screening, using the likelihood of disease. The in vitro tests may include one or more in vitro diagnostic tests measuring the concentrations of one or more biomolecules from patient-derived specimens to allow for diagnoses of diseases. Examples of biomolecules include proteins, peptides or metabolites from patient-derived specimens.

In block 140, the system 100 updates the likelihood of disease and stage. Updating the likelihood of disease may be based on the in vitro test results. The conditional probability Pr(A|B∩V) of occurrence of the disease A at a certain progression (stage) given the patient profile B and the in vitro diagnostic test results V may be expressed as Equation 2.

$$Pr(A \mid B \cap V) = \frac{Pr(B \cap V \mid A)Pr(A)}{Pr(B \cap V)}, \quad (2)$$

where Pr(B∩V|A) is the conditional probability of occurrence of the patient profile B and the in vitro test results V for the disease A, where Pr(A) is the probability of occurrence of the disease A across the population, and where Pr(B∩V) is the probability of occurrence of the patient profile B and the in vitro test results V across the population.

In block 145, the system 100 selects a medical test based on a combination of the patient information, in vitro test results, and medical information from a medical knowledge database 150. It is to be understood that a medical test may comprise various diagnostic medical procedures that are available for a disease of interest. For example, the selected medical test may include an endoscopic examination 167 and/or in vivo imaging 169. In the case of a colon/abdominal investigation, as shown in the dashed box 165 of FIG. 1, the medical test may include computed tomography (CT) colonoscopy, optical colonoscopy and/or positron emission tomography (PET)/CT colonoscopy.

Combining the in vitro test results and medical information from the medical knowledge database 150, according to Equation 2, gives a probability of disease Pr(A|B∩V). The probability of disease Pr(A|B∩V) may guide a physician in providing personalized medical diagnosis and treatment for a patient having the patient profile B and the in vitro test results V.

Figure 2:
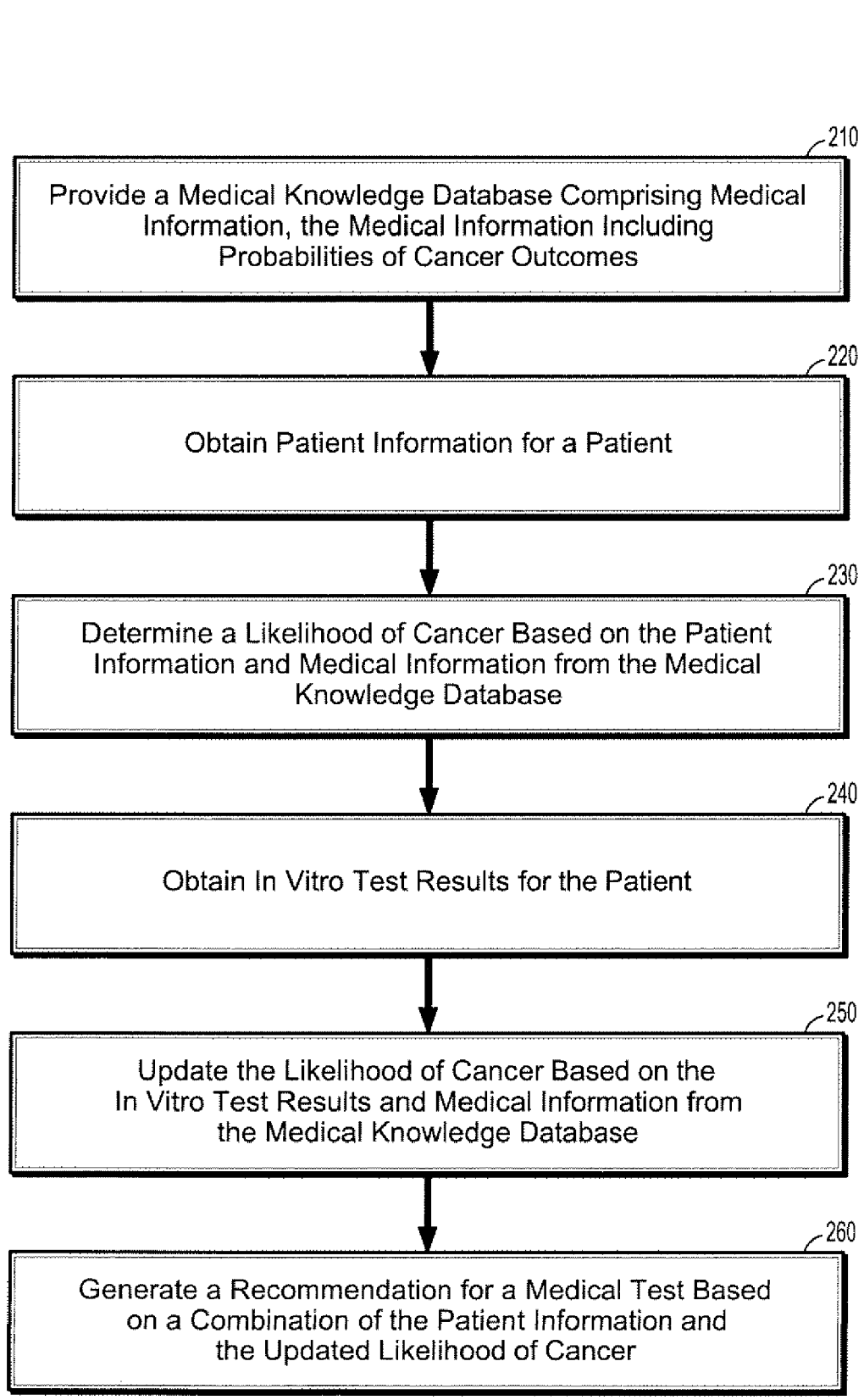
FIG. 2 is a flowchart showing a method of providing medical decision support for cancer diagnosis and treatment, according to an exemplary embodiment of the present invention.

FIG. 2 is a flowchart showing a computer-implemented method of providing medical decision support for cancer treatment and diagnosis, according to an exemplary embodiment of the present invention. Referring to FIG. 2, in block 210, provide a medical knowledge database comprising medical information, the medical information including probabilities of cancer outcomes.

In block 220, obtain patient information for a patient. The patient information may include age, ethnicity, family history of cancer, genetic markers and/or symptoms. The patient information may include physical and/or physiological findings.

In block 230, determine a likelihood of cancer based on the patient information and medical information from the medical knowledge database. For example, the patient information may be represented by the vector B, which is also referred to as patient profile B. For a certain stage of cancer, denoted as "C", the probability of occurrence of the cancer C characteristics across the population may be denoted as Pr(C). The conditional probability Pr(C|B) of occurrence of cancer C given the patient profile B may be expressed as Equation 3.

$$Pr(C \mid B) = \frac{Pr(B \mid C)Pr(C)}{Pr(B)}, \quad (3)$$

where Pr(B|C) is the conditional probability of occurrence of the patient profile B for cancer C, where Pr(C) is the probability of occurrence of cancer C across the population, and Pr(B) is the probability of occurrence of the patient profile B across the population.

In block 240, obtain in vitro test results for the patient. For example, the in vitro tests may include in vitro diagnostic tests measuring the concentrations of one or more biomolecules from patient-derived specimens to allow for diagnoses of diseases.

In block 250, update the likelihood of cancer based on the in vitro test results and medical information from the medical knowledge database. For example, the conditional probability Pr(C|B∩V) of occurrence of a certain stage of cancer C, given the patient profile B and the in vitro diagnostic test results V, may be expressed as Equation 4.

$$Pr(C \mid B \cap V) = \frac{Pr(B \cap V \mid C)Pr(C)}{Pr(B \cap V)}, \qquad (4)$$

where Pr(B∩V|C) is the conditional probability of occurrence of the patient profile B and the in vitro test results V for cancer C, where Pr(C) is the probability of occurrence of cancer C across the population, and where Pr(B∩V) is the probability of occurrence of the patient profile B and the in vitro test results V across the population.

In block 260, generate a recommendation for a medical test based on a combination of the patient information and the updated likelihood of cancer The patient information may include age ethnicity, family history of disease, genetic markers, symptoms, physical and/or physiological findings.

Although not shown as such in FIG. 2, a computer-implemented method of providing medical decision support for cancer diagnosis and treatment, according to an exemplary embodiment of the present invention, includes receiving results of the medical test and verifying the updated likelihood of cancer based on the in vitro test results and the medical test results. For example, the conditional probability Pr(C|V∩M) of occurrence of a certain stage of cancer C, given in vitro diagnostic test results V and the medical test results M, may be expressed as Equation 5.

$$Pr(C \mid V \cap M) = \frac{Pr(V \cap M \mid C)Pr(C)}{Pr(V \cap M)}, \qquad (5)$$

where Pr(V∩M|C) is the conditional probability of occurrence of the in vitro test results V and the medical test results M for cancer C, where Pr(C) is the probability of occurrence of cancer C across the population, and where Pr(V∩M) is the probability of occurrence of the in vitro test results V and the medical test results M across the population.

It is to be understood that exemplary embodiments of the present invention may be implemented in various forms of hardware, software, firmware, special purpose processors, or a combination thereof. For example, exemplary embodiments of the present invention may be implemented in software as an application program tangibly embodied on a program storage device. The application program may be uploaded to, and executed by, a machine comprising any suitable architecture.

Figure 3:
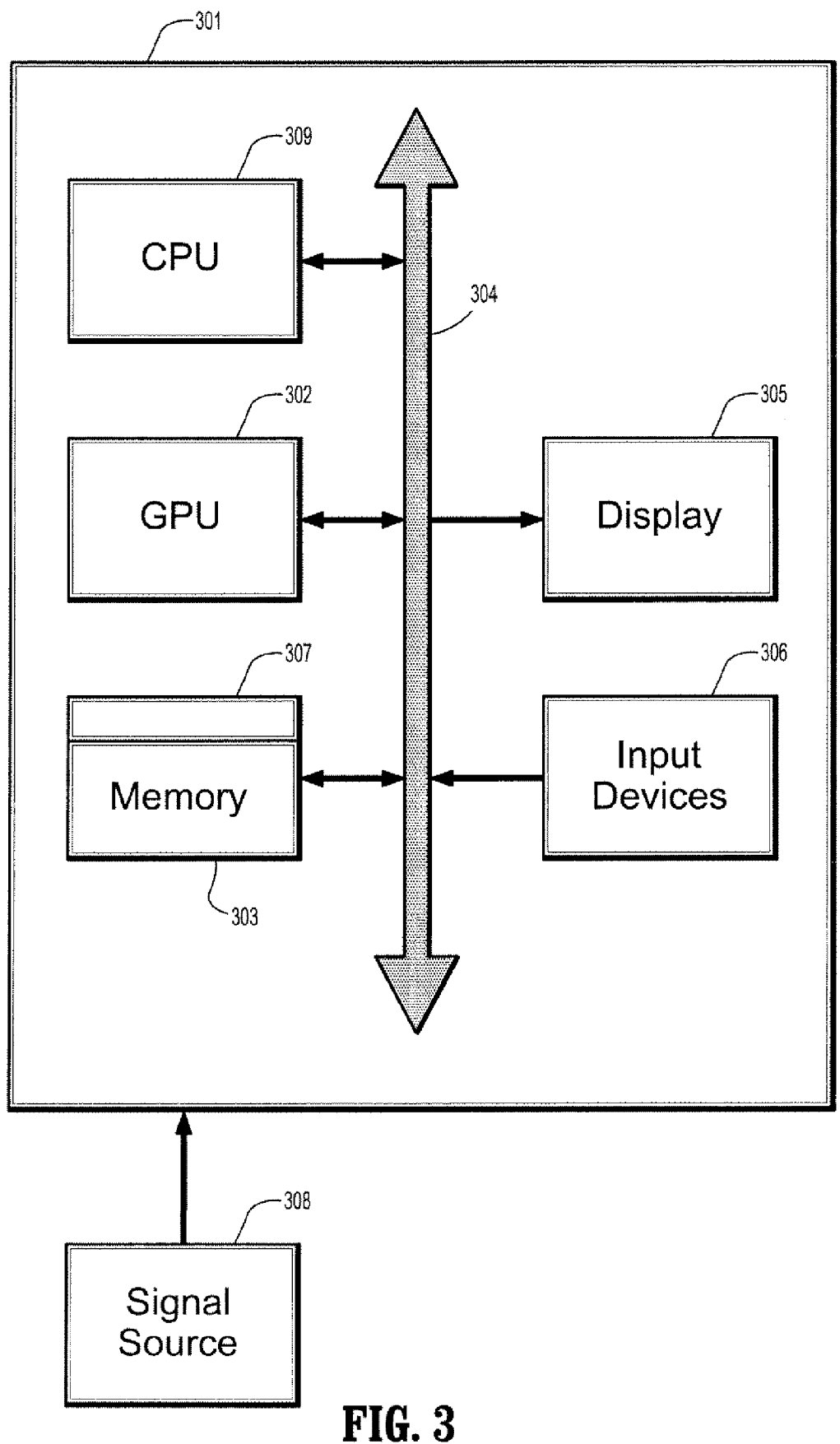
FIG. 3 illustrates a computer system for implementing a method of a method of providing medical decision support for cancer diagnosis and treatment, according to an exemplary embodiment of the present invention.

Referring to FIG. 3, according to an exemplary embodiment of the present disclosure, a computer system 301 for implementing a method of providing medical decision support for cancer diagnosis and treatment can comprise, inter alia, a central processing unit (CPU) 309, a memory 303 and an input/output (I/O) interface 304. The computer system 301 may include a graphics processing unit (GPU) 302. The computer system 301 is generally coupled through the I/O interface 304 to a display 305 and various input devices 306 such as a mouse and keyboard. The support circuits can include circuits such as cache, power supplies, clock circuits, and a communications bus. The memory 303 can include random access memory (RAM), read only memory (ROM), disk drive, tape drive, etc., or a combination thereof. An exemplary embodiment of the present invention can be implemented as a routine 307 that is stored in memory 303 and executed by the CPU 309 to process the signal from the signal source 308. As such, the computer system 301 is a general purpose computer system that becomes a specific purpose computer system when executing the routine 307 of the present invention.

The computer platform 301 also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

In an exemplary embodiment of the present invention, a system for providing medical decision support for cancer diagnosis and treatment comprises a medical knowledge database (not shown), a memory device 303 for storing a program, and a processor 309 in communication with the memory device 303. The processor 309 is operative with the program to obtain patient information for a patient, determine a likelihood of cancer based on the patient information and medical information from the medical knowledge database, obtain in vitro test results for the patient, update the likelihood of cancer based on the in vitro test results and medical information from the medical knowledge database, and automatically generate a recommendation for a medical test based on a combination of the patient information and the updated likelihood of cancer.

When determining the likelihood of cancer based on the patient information and medical information from the medical knowledge database, the processor 309 may be operative with the program to determine a ratio of: a conditional probability of occurrence of the patient information for a cancer type multiplied by the probability of occurrence of the cancer type across a population, with respect to the probability of occurrence of the patient information across the population. For example, the processor 309 may be operative with the program to apply Equation 3 to determine the likelihood of cancer based on the patient information.

When updating the likelihood of cancer based on the in vitro test results and medical information from the medical knowledge database, the processor 309 may be operative with the program to determine a ratio of: a conditional probability of occurrence of the patient information and the in vitro test results for a cancer type multiplied by the probability of occurrence of the cancer type across a population, with respect to the probability of occurrence of the patient information and the in vitro test results across the population. For example, the processor 309 may be operative with the program to apply Equation 4 to determine the likelihood of cancer based on the patient information and the in vitro test results.

It is to be further understood that, because some of the constituent system components and method steps depicted in the accompanying figures may be implemented in software, the actual connections between the system components (or the process steps) may differ depending upon the manner in which the present invention is programmed. Given the teachings of exemplary embodiments of the present invention provided herein, one of ordinary skill in the related art will be able to contemplate these and similar implementations or configurations of the present invention.

An integrative medical decision support system, according to an exemplary embodiment of the present invention, may enable patients, healthcare providers, biomedical researchers, and institutions to improve the diagnosis and treatment of disease. An integrative medical decision support system, according to an exemplary embodiment of the present invention, may accelerate the medical industry towards targeted therapies and personalized healthcare.

Although exemplary embodiments of the present invention have been described in detail with reference to the accompanying drawings for the purpose of illustration, it is to be understood that the inventive processes and systems are not to be construed as limited thereby. It will be readily apparent to one of ordinary skill in the art that various modifications to the foregoing exemplary embodiments can be made without departing from the scope of the invention as defined by the appended claims, with equivalents of the claims to be included therein.

What is claimed is:

1. A system for providing medical decision support for diagnosis and treatment of disease, comprising:
    a medical knowledge database comprising medical information, the medical information including probabilities of disease outcomes for a disease of interest;
    a memory device for storing a program;
    a processor in communication with the memory device, the processor operative with the program to:
    obtain patient information and in vitro test results for specimens derived from a patient; and
    automatically generate a recommendation for a medical test based on a combination of the patient information, the in vitro test results, and medical information from the medical knowledge database.

2. The system of claim 1, wherein the medical information further includes information selected from a plurality of case histories, randomized controlled trials, prospective longitudinal cohort studies, retrospective cohort studies, case control studies, cross sectional studies, case series, anecdotes or clinical observations.

3. The system of claim 1, wherein the medical information further includes information on diseases, conditions symptoms, medications, and treatment options and outcomes, risks, and benefit associated therewith.

4. The system of claim 1, wherein the patient information includes at least one of age, ethnicity, family history of disease, genetic marker, or symptoms.

5. The system of claim 1, wherein the in vitro test is selected from a plurality of in vitro diagnostic tests measuring the concentrations of one or more biomolecules from patient-derived specimens to allow for diagnoses of diseases.

6. The system of claim 1 wherein the medical test includes at least one of endoscopic examination, in vivo imaging, computed tomography (CT) colonoscopy, optical colonoscopy, or positron emission tomography (PET)/CT colonoscopy.

7. The system of claim 1, wherein when generating the recommendation for the medical test, the processor is further operative with the program to determine a probability of disease, wherein the probability of disease is a ratio of:
    a conditional probability of occurrence of the patient information for a disease of interest multiplied by the probability of occurrence of the disease of interest across a population, with respect to the probability of occurrence of the patient information across the population.

8. The system of claim 7, wherein the disease of interest is a cellular disease.

9. The system of claim 8, wherein the cellular disease is a cancer.

10. A computer-implemented method of providing medical decision support for cancer diagnosis and treatment comprising:
    providing a medical knowledge database comprising medical information, the medical information including probabilities of cancer outcomes;
    obtaining patient in information for a patient;
    determining a likelihood of cancer based on the patient information and medical information from the medical knowledge database;
    obtaining in vitro test results for specimens derived from the patient;
    updating the likelihood of cancer based on the in vitro test results and medical information from the medical knowledge database; and
    generating a recommendation for a medical test based on a combination of the patient information and the updated likelihood of cancer.

11. The computer-implemented method of claim 10, wherein the patient information includes at least one of age, ethnicity, family history of cancer, genetic markers, or symptoms.

12. The computer-implemented method of claim 10, wherein determining a likelihood of cancer comprises determining a ratio of a conditional probability of occurrence of the patient information for a cancer type multiplied by the probability of occurrence of the cancer type across a population, with respect to the probability of occurrence of the patient information across the population.

13. The computer-implemented method of claim 10, wherein the in vitro test is selected from a plurality of in vitro diagnostic tests measuring the concentrations of one or more biomolecules from patient-derived specimens to allow for diagnoses of diseases.

14. The computer-implemented method of claim 10, wherein updating the likelihood of cancer comprises determining a ratio of: a conditional probability of occurrence of the patient information and the in vitro test results for a cancer type multiplied by the probability of occurrence of the cancer type across a population, with respect to the probability of occurrence of the patient information and the in vitro test results across the population.

15. The computer-implemented method of claim 10, wherein the medical test includes at least one of endoscopic examination in vivo imaging computed tomography (CT) colonoscopy, optical colonoscopy, or positron emission tomography (PET)/CT colonoscopy.

16. The computer-implemented method of claim 10, further comprising receiving results of the medical test and verifying the updated likelihood of cancer based on the in vitro test results and the results of the medical test.

17. The computer-implemented method of claim 10, further comprising verifying the updated likelihood of cancer by determining a ratio of a conditional probability of occurrence of the in vitro test results and the medical test results for a cancer type multiplied by the probability of occurrence of the cancer type across a population, with respect to the probability of occurrence of the in vitro test results and the medical test results across the population.

18. A system for providing medical decision support for cancer diagnosis and treatment, comprising:
    a medical knowledge database comprising medical information, the medical information including probabilities of cancer outcomes;
    a memory device for storing a program;

a processor in communication with the memory device, the processor operative with the program to:

obtain patient information for a patient;

determine a likelihood of cancer based on the patient information and medical information from the medical knowledge database;

obtain in vitro test results for specimens derived from the patient;

update the likelihood of cancer based on the in vitro test results and medical information from the medical knowledge database; and automatically generate a recommendation for a medical test based on a combination of the patient information and the updated likelihood of cancer.

19. The system of claim 18, wherein the patient information include, at least one of age, ethnicity, family history of cancer genetic markers, or symptoms.

20. The system of claim 18, wherein the in vitro test is selected from a plurality of in vitro diagnostic tests measuring the concentrations of one or more biomolecules from patient-derived specimens to allow for diagnoses of diseases.

21. The system of claim 18, wherein the medical test includes at least on of endoscopic examination, in vivo imaging, computed tomography (CT) colonoscopy, optical colonoscopy, or positron emission tomography (PET)/CT colonoscopy.

22. The system of claim 18, wherein generating the recommendation for the medical test comprises determining a probability of cancer, and wherein the probability of cancer is a ratio of: a conditional probability of occurrence of the patient information for a cancer type multiplied by the probability of occurrence of the cancer type across a population, with respect to the probability of occurrence of the patient information across the population.

* * * * *